United States Patent [19]
Kelley

[11] Patent Number: 5,240,937
[45] Date of Patent: Aug. 31, 1993

[54] PHARMACEUTICALLY ACTIVE TRIAZOLOPYRIDINE COMPOUNDS

[75] Inventor: James L. Kelley, Raleigh, N.C.

[73] Assignee: Burroughs Wellcome Co., Research Triangle Park, N.C.

[21] Appl. No.: 877,660

[22] Filed: May 1, 1992

Related U.S. Application Data

[63] Continuation of Ser. No. 656,130, Feb. 14, 1991, abandoned, which is a continuation of Ser. No. 513,357, Apr. 20, 1990, abandoned.

[51] Int. Cl.$^5$ .................. A61K 31/435; C07D 471/04
[52] U.S. Cl. ..................................... 514/300; 546/117
[58] Field of Search ........................ 546/117; 514/300

[56] References Cited

U.S. PATENT DOCUMENTS 5,166,209  11/1992  Kelley ................................ 514/300

FOREIGN PATENT DOCUMENTS 1430288  10/1988  Australia .
0157637  10/1985  European Pat. Off. .
0288431  10/1988  European Pat. Off. .
2521920  12/1975  Fed. Rep. of Germany .

OTHER PUBLICATIONS

J. L. Kelley, et al., J. of Het. Chem., Jul.-Aug., 1986, pp. 1189–1193, vol. 23, Synthesis of 9-(2-Fluorobenzyl)-6-methylamino-9H-purine.

J. L. Kelley, et al., J. of Medicinal Chemistry pp. 1133–1134, 9-(2-Fluorobenzyl)-6-(methylamino) 9H-purine Hydrochloride. Synthesis and Anticonvulsant Activity (1986).

J. L. Kelley, et al., Journal of Medicinal Chemistry, 1988, vol. 31, No. 5, pp. 1005–1009, 9-(2-Fluorobenzyl)-6-(alkylamino)9H-purines. A New Class of Anticonvulsant Agents.

Woodbury, et al., Arch. int. pharmacodyn., 1952, XCII, No. 1, pp. 97–107 Design and Use of a New Electroshock Seizure Apparatus and Analysis of Factors Altering Seizure Threshold and Pattern (1).

Houston, et al., J. Med. Chem., 1985, 28, pp. 467–471, Potential Inhibitors of S-Adenosylmethionine-Dependent Methyltransferases. 8. Molecular Dissections of Carbocyclic 3-Deazaadenosine as Inhibitors of S-Adenosyl-homocystein Hydrolasse.

Chemical Abstracts CA52:9072D—B. W. Ashton and H. Suschitsky—carbazole synthesis of certain triazoles, none of which are encompassed by the general formula (1957).

J. L. Kelley, et al., J. of Het. Chemistry Jul.-Aug., 1988, pp. 1255–1258, vol. 25, Synthesis and Anticonvulsant Activity of 1-Benzyl-4-alkylamino-1H-imidazo [4,5-c]pyridines.

J. L. Kelley, et al., Journal of Medicinal Chemistry, 1988, vol. 31, No. 3, pp. 606–612, 6-(Alkylamino)-9-H-purines. A New Class of Anticonvulsant Agents.

*Primary Examiner*—Bernard Dentz
*Attorney, Agent, or Firm*—Donald Brown; Lawrence A. Nielsen; Robert T. Hrubiec

[57] ABSTRACT

This invention describes the preparation and use of anticonvulsant agents. In particular, triazolopyridine compounds are described which have utility in the treatment of epilepsy in mammals.

24 Claims, No Drawings

PHARMACEUTICALLY ACTIVE TRIAZOLOPYRIDINE COMPOUNDS

This application is a continuation of U.S. Ser. No. 07/656,130 filed Feb. 14, 1991, now abandoned, which is a continuation of U.S. Ser. No. 07/513,357 filed Apr. 20, 1990, now abandoned.

The present invention relates to triazolopyridines, to pharmaceutical compositions containing them, and to methods for their preparation, to their use in medicine and to methods of treating epilepsy in mammals.

European patent application no. 85302321.6, published under no. 157637 disclosed a class of 6-amino-9-(fluorobenzyl)-9H-purines as having anticonvulsant activity. 3-Deazapurines have also been reported (J. Heterocyclic Chem., 25, 1255, 1988) to have anticonvulsant activities.

European patent application no. 88810212.6, published under no. 0288431, discloses a class of 3H-1,2,3-triazolo[4,5-d]pyrimidines as anticonvulsant agents.

Epilepsy is a collective designation for a group of chronic central nervous system disorders having in common the occurrence of sudden and transitory episodes (seizure) of abnormal phenomena of motor (convulsions), sensory, autonomic or psychic origin. The seizures are nearly always correlated with abnormal electrical activity of the brain.

The incidence of epilepsy is estimated to be approximately 1% of the total world population. A fairly large proportion (10-20%) is not adequately controlled by currently available therapies; such patients are described as refractory. Those drugs which are currently available to the medical practitioner suffer from severe limitation in use and also have a number of side effects. It is therefore clearly apparent that there is a need for new antiepileptic drugs.

The present invention is directed to a series of novel triazolopyridines which have potent anticonvulsant activity.

Accordingly, in a first aspect of the present invention there is provided compound of formula I

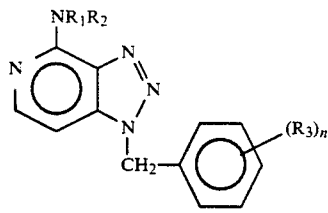

wherein $R_1$ and $R_2$ may be the same or different and are selected from hydrogen, $C_{1-4}$ straight or branched alkyl, $C_{3-4}$ cycloalkyl or cyclopropylmethyl; $R_3$ is hydrogen, or halo, preferably fluoro; and n is 1 or 2, provided that when $R_1$ and $R_2$ are selected from hydrogen or $C_{1-4}$ straight or branched chain alkyl then the phenyl ring is not substituted with fluoro at the 2 and 6 positions; or a salt, preferably pharmaceutically acceptable salt, thereof.

Particularly preferred compounds and salts thereof are those where $R_3$ is fluoro: more particularly when $R_3$ is selected from 2-fluoro; 3-fluoro; 4-fluoro; 2,5-difluoro; 2,4-difluoro; 2,3-difluoro; 3,4-difluoro and 3,5-difluoro.

The following compounds and their salts(preferably pharmaceutically acceptable) are particularly preferred:
1-(2-Fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]-pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]-pyridine,
1-(2,5-difluorobenzyl)-4-(methylamino)-1H-1,2,3-triazolo[4,5-c]-pyridine,
1-benzyl-4-(methylamino)-1H-1,2,3-triazolo[4,5-c]pyridine, and
4-(cyclopropylamino)-1-(2,6-difluorobenzyl)-1H-1,2,3-triazolo[4,5-c]-pyridine Suitable acid addition salts of the compounds of formula I include those formed with both organic and inorganic acids. Such acid addition salts will normally be pharmaceutically acceptable.

Thus, preferred salts include those formed from hydrohalic, e.g., hydrochloric, sulphuric, citric, isethionic, tartaric, phosphoric, lactic, pyruvic, acetic, succinic, oxalic, fumaric, maleic, lactobionic, oxaloacetic, methanesulphonic, p-toluenesulphonic and benzenesulphonic acids.

There is also provided the first medical use of the novel compounds of the present invention or pharmaceutically acceptable salts thereof, as hereinbefore defined. Preferably this will be for the treatment of epilepsy, e.g., in mammals such as humans. The compounds of the present invention have phenytoin like activity and should be particularly useful in the treatment of primary generalised tonic-clonic (grand mal) epilepsy.

In a further aspect, there are provided pharmaceutical formulations comprising a compound of the present invention in admixture with a pharmaceutically acceptable carrier.

The pharmaceutically acceptable carriers present in the compositions of this invention are materials recommended for the purpose of administering the medicament. These may be liquid or solid materials, which are otherwise inert or medically acceptable and are compatible with the active ingredients.

These pharmaceutical compositions may advantageously be given orally, but may also be given parenterally, used as a suppository, or applied topically as an ointment, cream or powder. Oral and parenteral administration of the compositions are preferred.

For oral administration, fine powders or granules will contain diluting, dispersing and/or surface active agents, and may be presented in a draught, in water or in a syrup, in capsules or sachets in the dry state or in non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain anti-oxidants or buffers.

As stated above, the free base or a salt thereof may be administered in its pure form unassociated with other derivatives, in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch or calcium phosphate for tablet or capsule; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of a novel compound as hereinbefore defined which is effective at such dosage or a multiple of the same, for instance, units containing 5 mg to 500 mg, usually around 10 mg to 250 mg.

The pharmaceutical compositions of the present invention will be prepared by the admixture of a novel compound or a pharmaceutically acceptable salt thereof as hereinbefore defined with a pharmaceutically acceptable carrier. Conventional pharmaceutical excipients may be admixed as required.

The present invention provides a method of treatment of CNS disorders such as convulsions, particularly epilepsy, in mammals by the administration of a non-toxic therapeutically effective amount of a compound of the formula I or a pharmaceutically acceptable salt, or a composition as hereinbefore defined.

Preferably the mammal is a human.

Before commencement of the treatment the mammal in question will, in general, have been identified as suffering from a CNS disorder, particularly epilepsy.

Thus in a preferred embodiment of the present invention, there is provided a method of treatment of epilepsy in humans, comprising the administration to a human in need thereof or a non-toxic therapeutically effective amount of a compound of the formula I or a pharmaceutically acceptable salt, or a composition as hereinbefore defined.

As indicated above, the compounds of the formula I are generally useful in treating such disorders by administration to the human or animal recipient by a route selected from oral, parenteral (including subcutaneous, intradermal, intramuscular and intravenous) and rectal. The size of an effective dose of a compound will depend upon a number of factors including the mammal under treatment (for example cat, dog or human), the type of epilepsy involved for example grand mal, focal seizures and psychomotor convulsions, the severity of the condition to be treated and the route of administration, and will ultimately be at the discretion of the attendant physician. In guiding him in assessing the efficacy and acceptability of a regimen the physician will have recourse to changes in the recipient's gross condition as treatment progresses.

Such an effective epileptic treatment dose is in the range 0.3 to 15 mg/kg bodyweight of animal or human recipient given three times per day, preferably in the range 0.5 to 7 mg/kg bodyweight and most preferably in the range of 1 to 2 mg/kg bodyweight. For the average human of 70 kg bodyweight at 1.0 mg/kg the dose would be 70 mg. Unless otherwise indicated all weights are calculated as the hydrochloride of formula I. For other salts the figures would be amended proportionately. The desired dose may be preferably presented as between two and four sub-doses administered at appropriate intervals throughout the day.

The present invention also provides a process for the preparation of a compound of formula I, which process comprises the reaction of an amine $HNR_1R_2$ with a compound of formula II

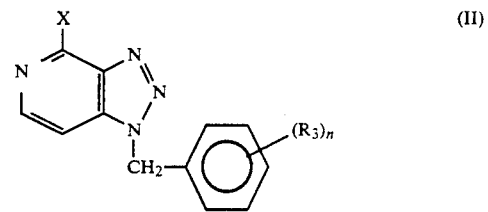

(II)

where $R_1$, $R_2$ and $R_3$ and n are as hereinbefore defined and X is a leaving group.

Compounds of formula II can be prepared by reacting the appropriate diaminopyridines of formula III

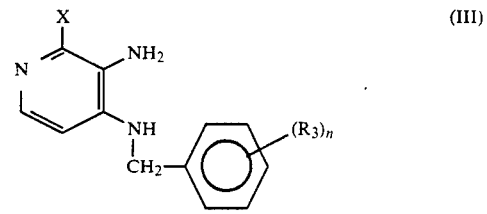

(III)

where X and $R_3$ and n are as hereinbefore defined with sodium nitrite in hydrohalic acid, particularly hydrochloric acid.

Compounds of formula III can be prepared by reductive halogenation of a compound of formula IV

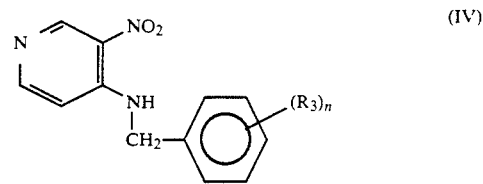

(IV)

wherein $R_3$ and n are as hereinbefore defined by treating, for example, with stannous chloride in hot concentrated hydrochloric acid.

Compounds of formula IV can be prepared by reacting compounds of formula wherein $R_4$ is halogen, preferably chloro, or OR where R is $C_{1-6}$ alkyl, preferably ethyl,

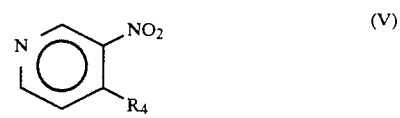

(V)

with the appropriate benzyl amine.

Compounds of formula V can be prepared from 4-hydroxypyridine by nitrating with fuming nitric acid and reacting the resulting 4-hydroxy-3-nitropyridine with phosphorous pentachloride, followed by reaction with an appropriate alcohol.

The reaction of a compound of formula II with a mono or disubstituted amine will take place in any suitable solvent, preferably this will be a polar solvent such as a $C_{1-4}$ alkanol, water or acetonitrile. Where appropriate the amine may be used as co-solvent. The reaction will be carried out at non-extreme temperatures, e.g., 0°–180° C. suitably at 15°–120° C. and conveniently at room temperature.

Suitable leaving groups X include halogen, $C_{1-6}$ alkylthio, $C_{6-10}$ arylthio, $C_{7-12}$ aralkylthio or $C_{1-4}$ alkyl-, phenyl-, benzyl-, phenylethyl- or naphthylmethyl-substituted sulphonyl or sulphinyl. Preferred leaving groups include halogen, particularly chlorine.

Alternatively compounds of formula II can be prepared by the reaction of a compound formula VI with a compound of formula VII (Aldrich)

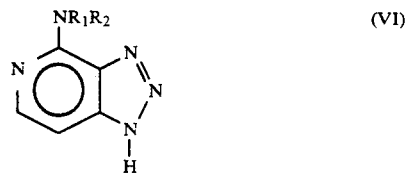

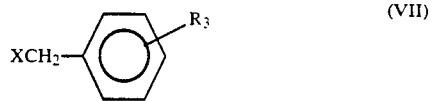

wherein $R_1$ $R_2$ $R_3$ and X are hereinbefore defined.

The triazolo[4,5-c] pyridines of formula (VI) can be prepared in a manner analogous to the preparation of formula (II) by reacting a compound of formula VIII

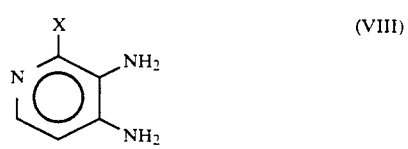

with sodium nitrite in hydrohalic acid and corresponding amination, with suitable aminating agents.

The following examples serve to illustrate the present invention, and should not be construed as limiting thereof.

EXAMPLE 1

Preparation of 1-(2-fluorobenzyl)-4-(methylamino)-1H-1,2,3-triazolo[4,5-c]pyridine

A. Preparation of 4-[(2-fluorobenzyl)amino]-3-nitropyridine

A mixture of 4-chloro-3-nitropyridine[1] (22.19 g, 0.140 mol). 2-fluoro-benzylamine (Aldrich) (16.04 g, 0.128 mol) and water/dioxane (8:3) (220 ml) was stirred at ambient temperature for 30 min. The reaction mixture was cooled in an ice-bath and triethylamine (107 ml) was added dropwise. A precipitate formed, and the mixture was stirred for 30 min at ice bath temperature and at ambient temperature for 15 hr. The suspension was diluted with water (300 ml). The solids were collected, dried, dissolved in dichloromethane and added to Silica Gel 60. This mixture was spin evaporated in vacuo, and the residual solids were added to a column (5 cm × 25 cm) of Silica Gel 60 wetted with dichloromethane/ethyl acetate (5:1). The column was eluted with the same solvent using the flash chromatography technique. The appropriate fractions were combined and spin evaporated in vacuo to give 25.5 g (80%) of 4-[(2-fluorobenzyl)amino]-3-nitropyridine as a bright yellow solid, mp.=108°–109°; UV (0.1N hydrochloric acid+5% methanol) λmax 231 nm (ξ16600), 268 nm (ξ14700), 345 nm (ξ4200); pH 7.0 buffer +5% methanol) λmax 237 nm (ξ22600), 378 nm (ξ5900); (0.1N sodium hydroxide+5% methanol) λmax 237 nm (ξ20500), 378 nm (ξ5400); 1H nmr (DMSO-$d_6$): δ9.05 (s, 1H, pyridine H-2), 8.89 (t, 1H,NH), 8.22 (d,1H,J=6 Hz, pyridine H-6), 7.4–7.1 (m, 4H,Ar), 6.84 (d,1H,J=6 Hz, pyridine H-5), 4.71 (d,2H,J=6 Hz, $CH_2$).

1. D. M. Houston, E. K. Dolence, B. T. Keller, U. P.-Tombre and R. T. Borchard, *J. Med. Chem.*, 31, 467 (1985).

B. Preparation of 3-amino-2-chloro-4-[(2-fluorobenzyl)amino]pyridine

A mechanically stirred solution of 4-[(2-fluorobenzyl)amino]-3-nitropyridine (12.31 g, 49.8 mmol) in concentrated hydrochloric acid (118 ml) was heated to 90° under a nitrogen atm. Stannous chloride dihydrate (55.56 g, 246 mmol) was added in small portions over a 5 min period (the oil bath was removed until the reaction subsided). After an additional 30 min at 90°, the reaction mixture was cooled, diluted with water (200 ml) and spin evaporated in vacuo. The residue was diluted with water (200 ml) and cooled in an ice-bath, while concentrated ammonium hydroxide was added to adjust the pH to 7–8. The solids were collected and allowed to air dry overnight. The solid was treated with ethyl acetate and filtered (12×200 ml), the combined extracts were washed with water, dried (sodium sulphate) and spin evaporated in vacuo. The residue was combined with the product from a separate reaction (12 g, 48.5 mmoles) and dissolved in ethyl acetate. This solution was added to Silica Gel 60 and spin evaporated in vacuo. The residual solids were introduced to a column (5 cm×30 cm) of Silica Gel 60 wetted with ethyl acetate. The column was eluted with ethyl acetate using flash chromatography. The appropriate fractions were combined and spin evaporated in vacuo to give 20.8 g (84%) of 3-amino-2-chloro-4-[2-fluorobenzyl)amino]-pyridine as a white solid, mp.=185°–187°; UV (0.1M hydrochloric acid+5% methanol), λmax 233 nm (ξ17900), 302 nm (ξ14900); (pH 7.0 buffer+5% methanol), λmax 262 nm (ξ11200), (0.1N sodium hydroxide+5% methanol), λmax 262 nm (ξ10700), 1H nmr (DMSO-$d_6$): δ7.36–7.15 (complex m, 5H,Ar+pyridine H-6), 6.35–6.30 (d,1H,pyridine H-5), 6.27–6.33 (overlapping,1H,NH). 4.84 (2,2H,$NH_2$). 4.41 (d,2H,J=5 Hz, $CH_2Ar$).

B(i). Alternative preparation of 3-amino-2-chloro-4-[(2-fluorobenzyl)amino]pyridine A mechanically stirred solution of 4-[(2-fluorobenzyl)amino]-3-nitropyridine (37.62 g, 152.17 mmol) in concentrated hydrochloric acid (400 mL) was heated to 90° under a nitrogen atmosphere. Stannous chloride dihydrate (174.88 g, 775.07 mmol) was added in small portions over a 20 min period. When the reaction became vigorous, the oil bath was removed until the reaction subsided. After 45 min at an increased temperature to 120° for 45 min, the reaction mixture was cooled, diluted with water (350 mL) and spin evaporated in vacuo. The residue was diluted with water (600 mL), cooled in an ice-bath and concentrated ammonium hydroxide (250 mL) was added to adjust the pH to 7–8.

The solid were collected and allowed to air dry overnight. The solid cake was broken up and suspended in ethyl acetate (3×1 L). Each suspension was refluxed with the refluxing time varying from 3.5 hrs to 18 hrs. The ethyl acetate was filtered and evaporated in vacuo to yield 3-amino-2-chloro-4-[(2-fluorobenzyl)amino]pyridine (27.13 g, 71%) as an off-white solid, mp.=181°-187°. The analytical sample was prepared by essentially the same preparative method and was purified by column chromatography.

C. Preparation of 1-(2-fluorobenzyl)-4-(methylamino)-1H-1,2,3-triazolo[4,5-c]pyridine hydrochloride To an ice cold solution of 3-amino-2-chloro-4-[(2-fluorobenzyl)amino]pyridine (4.0 g, 15.9 mmol), 1N hydrochloric acid (40 ml), concentrated hydrochloric acid (15 ml) and ethanol (120 ml) was added sodium nitrite (1.31 g, 18.9 mmol). The solution was stirred for 15 min and 40% aqueous methylamine (100 ml) was added. The solution was refluxed with stirring for 30 min. The reaction was cooled, and the solid was collected and washed with water. The solid was dissolved in hot ethanol (155 ml) and then diluted with concentrated hydrochloric acid (55 ml). The solution was cooled and the white solid was collected to give 3.72 g (79%) of 1-(2-fluorobenzyl)-4-(methylamino)-1H-1,2,3-triazolo[4,5-c]pyridine hydrochloride, mp=280°-282° C. (dec); UV (0.1N hydrochloric acid+5% methanol) $\lambda$max 280 nm ($\xi$12900); (pH 7.0 buffer+5% methanol) $\lambda$max 302 nm ($\xi$8600); (0.1N sodium hydroxide+5% methanol) $\lambda$max 306 nm ($\xi$9000); 1H nmr (DMSO-$d_6$): $\delta$10.2 (br m, 1H, NH), 7.84 (d, 1H, J=7 Hz, pyridine H-6), 7.5-7.2 (m, 5H, Ar+pyridine H-7), 6.03 (s, 2H, $CH_2$), 3.13 (br, s, 3H, $CH_3$).

EXAMPLE 2

Preparation of 4-(cyclopropylamino)-1-(2-fluorobenzyl)-1H-1,2,3-triazolo[4,5-c] pyridine This compound was prepared in an analogous manner to that of example 1 with the replacement of methylamine in example 1 C with cyclopropylamine. It was precipitated from free base in EtOH with concentrated HCl. Yield 72%, mp=245°-247° C. UV: (0.1N HCl) $\lambda$max 283 ($\xi$13800); (pH 7 buffer) $\lambda$max 300 ($\xi$9400); (0.1N NaOH) $\lambda$max 306 ($\xi$10000).

EXAMPLE 3

Preparation of 4-(ethylamino)-1-(2-fluorobenzyl)-1H-1,2,3-triazolo[4,5-c]pyridine This compound was prepared in an analogous manner to that of example 1 with the replacement of methylamine in example 1 C with ethylamine. The compound was precipitated from a solution of the free base in EtOH with concentrated HCl. Yield 84%, mp. =258-260 UV:(0.1N HCl) $\xi$max 282.8 nm ($\xi$13400); (pH 7 buffer) $\lambda$max 306.8 ($\xi$9400); (0.1N NaOH) $\lambda$max 308.8 ($\xi$9700).

EXAMPLE 4

Preparation of 4-(dimethylamino)-1-(2-fluorobenzyl)-1H-1,2,3-triazolo[4,5-c]pyridine This compound was prepared in an analogous manner to the compound in example 1 with the replacement of methylamine in example 1 C with dimethylamine. The compound was recrystallised from propan-2-ol. Yield 69%, mp.=248°-252° UV:(0.1N HCl) $\lambda$max 289.6 ($\xi$15200); (pH 7 buffer) $\lambda$max 318.0 ($\xi$10600); (0.1N NaOH) $\lambda$max 318.0 ($\xi$11900).

EXAMPLE 5

Preparation of 1-(2,5-difluorobenzyl)-4-(methylamino)-1H-1,2,3-triazolo[4,5-c]pyridine

A. Preparation of 4-[(2,5-difluorobenzyl)amino]-3-nitropyridine.

This compound was prepared in a manner analogous to example 1A, but replacing 2-fluorobenzylamine with 2,5-difluorobenzylamine, (Aldrich).

B. Preparation of 3-amino-2-chloro-4-[(2,5-difluorobenzyl)amino]pyridine

This compound was prepared in a manner analogous to the compound of 18 but replacing 4-[(2-fluorobenzyl)amine]-3-nitropyridine with the title compound from example 5A.

C. Preparation of 1-(2,5-difluorobenzyl)-4-(methylamino)-1H-1,2,3-triazolo[4,5-c]pyridine This compound was prepared in an analogous manner to the compound of 1 C using methylamine and 3-amino-2-chloro-4-[(2,5-difluorobenzyl)amino]pyridine as starting material. It was precipitated from a solution of the free base in EtOH with concentrated HCl. Yield 88% mp=273°-278°.

UV: (0.1N HCl) $\lambda$max 275.6 ($\xi$15000); (pH 7 buffer) $\lambda$max 275.2 ($\xi$6800) $\lambda$max 304.8 ($\xi$9100); (0.1N NaOH) $\lambda$max 275.2 ($\xi$5700) $\lambda$max 308.4 ($\xi$8800).

EXAMPLE 6

Preparation of 1-benzyl-4-(methylamino)-1H-1,2,3-triazolo[4,5-c]pyridine

A. Preparation of 4-(benzylamino)-3-nitropyridine

This compound was prepared in a manner analogous to example 1A, but replacing 2-fluorobenzylamine with benzylamine, (Aldrich).

B. Preparation of 3-amino-2-chloro-4-(benzylamino)pyridine

This compound was prepared in a manner analogous to the compound 1 C, but replacing 4-(2-fluorobenzyl)amino-3-nitropyridine with the title compound from example 6A.

C. Preparation of 1-benzyl-4-(methylamino)-1H-1,2,3-triazolo[4,5-c]pyridine This compound was prepared in an analogous manner to the compound of 1 C using methylamine and 3-amino-2-chloro-4-[(benzylamino)]pyridine as starting materials. It was recrystallised from water with concentrated HCl. Yield 39%. mp=269°-273°. UV:(0.1N Hcl) $\lambda$max 280.0 ($\xi$10900); (pH 7 buffer) $\lambda$max 302.8 ($\xi$7400); (0.1N NaOH) $\lambda$max 306.4 ($\xi$8000).

EXAMPLE 7

Preparation of 4-(cyclopropylamino)-1-(2,6-difluorobenzyl)-1H-1,2,3-triazolo[4,5-c]pyridine Preparation of 3-nitro-4-[(2,6-difluorobenzyl)amino]pyridine Reaction:

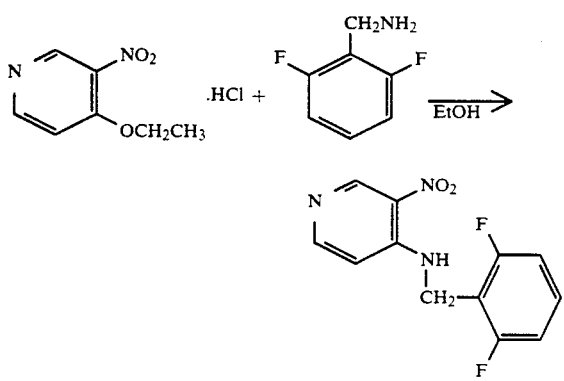

Procedure: A 2 L Erlenmyer flask, equipped with a magnetic stirrer, was charged with sodium hydroxide and methylene chloride (800 mL). With rapid stirring, 4-ethoxy-3-nitropyridine hydrochloride[1] was added portionwise over 10 minutes. The biphase mixture was stirred an additional 10 minutes, transferred to a 3 L separatory funnel and the organic layer separated. The aqueous portion was extracted with methylene chloride (800 mL) and the combined organic extracts were concentrated to dryness in vacuo to yield the free base as a tan solid (175 g, 104%) which was used without further purification.

1. 4-Ethoxy-3-nitropyridine hydrochloride was prepared according to the literature produced of J. B. Campbell al (J. Heterocyclic. Chem., 1986 23, 669). The compound is more stable as the hydrochloride salt and is neutralised immediately before use.

A one-neck 3L flask, equipped with a reflux condenser, magnetic stirrer, and nitrogen inlet was charged with freshly prepared 4-ethoxy-3-nitropyridine, 2,6-difluorobenzylamine[2] and absolute ethanol (1.9 L). The solution was heated at reflux for 20 h, cooled slightly, poured into an Erlenmyer flask and refrigerated overnight. The resulting yellow precipitate was collected by filtration, washed with chilled ethanol (150 mL) and dried on a Buechner funnel to yield 234 g (88.4%) of 3-nitro-4-[(2,6-difluorobenzyl)amino]pyridine: TLC (silica gel, EtOAc/Hexane, 1:1) $R_f$=0.31; MP=148°-149° C.; 1H NMR (DMSO-$d_6$) δ5.74 (d,J=5.7 Hz, 2H, $CH_2$), 7.01 (d, J=6.3 Hz, 1H, C-5H), 7.14 (m, 2H, C-3'H and C-5'H), 7.44 (m, 1H, C-4'H), 8.32 (d, J=6.2 Hz, 1H, C-6H), 8.65 (t, J=6.0 Hz, 1H, NH) and 9.03 (s, 1H, C-2H). Elemental Analysis calculated C, 54.35; H, 3.42; N, 15.84; F, 14.33; Found, C. 54.40; H, 3.44; N, 15.85; F, 14.21.

2. 2,6-Difluorobenzylamine is commercially available but was prepared from a $BH_3$·THF reduction of 2,6-difluorobenzonitrile. The product contained 23% (wt) of 1-butanol by $^1H$ NMR and this is factored into the quantity of 2,6-difluorobenzylamine employed.

Preparation of 4-(cyclopropylamino)-1-(2,6-difluorobenzyl)-1H-1,2,3-triazolo[4,5-c]pyridine This compound was prepared in an analogous manner to that of Example 1 with the replacement of 2-fluorobenzylamine in Example 1A with 2,6-difluorobenzylamine(Aldrich) and of methylamine in example 1C with cyclopropylamine. It was precipitated from the free base in EtOH with concentrated HCl. mp>260° C. (dec). UV:(0.1N HCl) λmax 286 (ξ14200); (pH 7 buffer) λmax 306 (ξ9900); (0.1N NaOH) λmax 309 (ξ10000).

Pharmacological Activity

The anticonvulsant activity of certain compounds of the present invention were determined by a standard maximal electroshock test (MES); that described by L. A. Woodbury and V. D. Davenport, Arch. Int. Pharmacodyn, 1952 92 97.

| COMPOUND OF EXAMPLE NO | SALT | ED50.P.O. (mg/kg) |
|---|---|---|
| 1 | HCl | 4.4 |
| 2 | HCl | 6.3 |
| 3 | HCl | 10.3 |
| 4 | HCl | 6.6 |
| 5 | HCl | 4.3 |
| 6 | HCl | 8.9 |
| 7 | HCl | 8.1 |

FORMULATION EXAMPLES

In the formulation examples that follow, the active ingredients are compounds hereinbefore defined by formula I.

I—Formulation

| | |
|---|---|
| Active ingredient | 25 mg |
| Corn starch | 45 mg |
| Polyvinylpyrrolidone | 6 mg |
| Stearic acid | 12 mg |
| Magnesium stearate | 2 mg |
| Lactose qs to | 300 mg |

The active ingredient is finely ground and intimately mixed with the powdered excipients lactose and corn starch. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 300 mg each.

II—Capsule

| | |
|---|---|
| Active ingredient | 25 mg |
| Corn starch | 45 mg |
| Stearic acid | 12 mg |
| Lactose qs to | 300 mg |

The finely ground active ingredient is mixed with the powdered exipients lactose and corn starch, and stearic acid and filled into hard-shell gelatin capsules.

III—Suppository

| | |
|---|---|
| Active ingredient | 25 mg |
| Cocoa butter | 1975 mg |

The cocoa butter is heated to melting and the active ingredient is dispersed by thorough mixing. The mass is then formed into suppositories weighing approximately 2,000 mg each.

IV—Injection

| Active ingredient | 25 mg |
|---|---|
| Sodium chloride | 0.9% |
| Preservative | 0.1% |
| Hydrochloric acid or sodium hydroxide | as need for pH adjustment |
| Water for injection | qs to 2-3 ml. |

The active ingredient, sodium chloride, and preservative are dissolved in a portion of the water for injection. The pH of the solution is adjusted with hydrochloric acid or sodium hydroxide. Water for injection is added to final volume and the solution is thoroughly mixed. The solution is sterilized by filtration through a 0.22 micrometer membrane filter and aseptically filled into sterile containers.

V—Syrup

| Active ingredient | 15 mg |
|---|---|
| Glycerin | 500 mg |
| Sucrose | 3500 mg |
| Flavouring agent | qs |
| Colouring agent | qs |
| Preserving agent | 0.1% |
| Purified water | qs to 5 ml |

The active ingredient and sucrose are dissolved in the glycerin and a portion of the purified water. The preserving agent is dissolved in another portion of hot purified water, and then the colouring agent is added and dissolved. The two solutions are mixed and cooled before the flavouring agent is added. Purified water is added to final volume. The resulting syrup is thoroughly mixed.

What I claim is:

1. A compound of formula I wherein $R_1$ and $R_2$ may be the same or different and are selected from hydrogen and $C_{1-4}$ straight or branched alkyl, $C_{3-4}$ cycloalkyl or cyclopropylmethyl; $R_3$ is hydrogen, or halo and n is 1 or 2, provided that when $R_1$ and $R_2$ are selected from hydrogen or $C_{1-4}$ straight or branched chain alkyl then the phenyl ring is not substituted with fluoro at the 2 and 6 positions; or a salt thereof.

2. The compound of claim 1 wherein $R_1$ is hydrogen.

3. The compound of claim 1 or 2 wherein the salt is a pharmaceutically acceptable salt.

4. The compound of claim 1 or 2 wherein the salt is a pharmaceutically acceptable acid addition salt.

5. The compound of claim 3 wherein the salt is the hydrochloride salt.

6. A compound of claim 1 which is selected from
1-(2-fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]pyridine
1-(2,5-difluorobenzyl)-4-(methylamino)-1H-1,2,3-triazolo[4,5-c]pyridine, 1-benzyl-4-(methylamino)-1H-1,2,3-triazolo[4,5-c]pyridine, and
4-(cyclopropylamino)-1-(2,6-difluorobenzyl)-1H-1,2,3-triazolo[4,5-c]pyridine, or a pharmaceutically acceptable acid addition salt thereof.

7. A compound of claim 6 wherein the salt is the hydrochloride salt.

8. A pharmaceutical formulation comprising a compound of formula I wherein $R_1$ and $R_2$ may be the same or different and are selected from hydrogen and $C_{1-4}$ straight or branched alkyl, $C_{3-4}$ cycloalkyl or cyclopropylmethyl; $R_3$ is hydrogen, or halo; and n is 1 or 2, provided that when $R_1$ and $R_2$ are selected from hydrogen or $C_{1-4}$ straight or branched chain alkyl then the phenyl ring is not substituted with fluoro at the 2 and 6 positions; or a pharmaceutically acceptable salt thereof and a pharmaceutically acceptable carrier therefor.

9. A pharmaceutical formulation of claim 8 wherein $R_1$ is hydrogen.

10. A pharmaceutical formulation of claim 8 wherein the compound is
1-(2-Fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]pyridine,
1-(2,5-difluorobenzyl)-4-(methylamino)-1H-1,2,3-triazolo[4,5-c]pyridine, 1-benzyl-4-(methylamino)-1H-1,2,3-triazolo[4,5-c]pyridine, or
4-(cyclopropylamino)-1-(2,6-difluorobenzyl)-1H-1,2,3-triazolo[4,5-c]pyridine, or a pharmaceutically acceptable acid addition salt thereof.

11. The pharmaceutical formulation of claim 10 wherein the salt is the hydrochloride salt.

12. A pharmaceutical formulation of claim 10 which is a tablet or capsule.

13. A method of treating a mammal which has been identified as having had convulsions which comprises administering an effective anticonvulsant amount of a pharmaceutical formulation as defined in claim 8.

14. The method of claim 13 which comprises the oral administration of a tablet or capsule containing
1-(2-fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]pyridine,
1-(2,5-difluorobenzyl)-4-(methylamino)-1H-1,2,3-triazolo[4,5-c]pyridine, 1-benzyl-4-(methylamino)-1H-1,2,3-triazolo[4,5-c]pyridine, or
4-(cyclopropylamino)-1-(2,6-difluorobenzyl)-1H-1,2,3-triazolo[4,5-c]pyridine, or a pharmaceutically acceptable salt thereof.

15. The method of claim 13 which comprises the parenteral administration of
1-(2-fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]pyridine,
1-(2,5-difluorobenzyl)-4-(methylamino)-1H-1,2,3-triazolo[4,5-c]pyridine, 1-benzyl-4-(methylamino)-1H-1,2,3-triazolo[4,5-c]pyridine, or 4-(cyclopropylamino)-1-(2,6-difluorobenzyl)-1H-1,2,3-triazolo[4,5-c]pyridine, or a pharmaceutically acceptable salt thereof.

16. The method of claim 13 wherein said mammal is a human.

17. A method of treating epilepsy in a human which comprises administering to said human a therapeutically effective amount of
1-(2-fluorobenzyl)-4-(methylamino)-1H-1,2,3-triazolo[4,5-c]pyridine,
4-(cyclopropylamino)-1-(2-fluorobenzyl)-1H-1,2,3-triazolo[4,5-c]pyridine,
4-(ethylamino)-1-(2-fluorobenzyl)-1H-1,2,3-triazolo[4,5-c]pyridine,
4-(dimethylamino)-1-(2-fluorobenzyl)-1H-1,2,3-triazolo[4,5-c]pyridine,
1-(2,5-difluorobenzyl)-4-(methylamino)-1H-1,2,3-triazolo[4,5-c]pyridine, 1-benzyl-4-(methylamino)-1H-1,2,3-triazolo[4,5-c]pyridine, or
4-(cyclopropylamino)-1-(2,6-difluorobenzyl)-1H-1,2,3-triazolo[4,5-c]pyridine, or a pharmaceutically acceptable salt thereof.

18. A method of treating epilepsy in a mammal, which comprises administering to a mammal an effective epilepsy treatment amount of the compound or salt of claim 1.

19. The compound or salt of claim 1, in which $R_3$ is fluoro.

20. A pharmaceutical composition for the treatment of epilepsy comprising an effective epilepsy treatment amount of the compound or salt of claim 1 or 6 in a pharmaceutically acceptable carrier.

21. 4-(cyclopropylamino)-1-(2-fluorobenzyl)-1H-1,2,3-triazalo [4,5-c]pyridine or a pharmaceutically acceptable acid addition salt thereof.

22. 4-(cyclopropylamino)-1-(2,6-difluorobenzyl)-1H-1,2,3-triazalo [4,5-c] pyridine or a pharmaceutically acceptable acid addition salt thereof.

23. The method of treating convulsions comprising administering to a mammal in need thereof an effective anticonvulsant amount of the compound of claim 21 or 22.

24. A unit dose of a formulation of claim 8 containing 5 to 500 mg of a compound of formula (I) or a pharmaceutically acceptable salt thereof in the form of a tablet or capsule.

* * * * *